United States Patent [19]
Frey et al.

[11] Patent Number: 5,133,767
[45] Date of Patent: Jul. 28, 1992

[54] PROSTHESIS HAVING A DEFORMABLE IMPLANT SURFACE

[75] Inventors: Otto Frey, Winterthur; Rudolf Koch, Berlingen; Hans Fluckiger, Willikon, all of Switzerland

[73] Assignee: Sulzer Brothers Limited, Winterthur, Switzerland

[21] Appl. No.: 585,473

[22] Filed: Sep. 20, 1990

[30] Foreign Application Priority Data

Oct. 12, 1989 [CH] Switzerland ............... 3719/89

[51] Int. Cl.⁵ .............................. A61F 2/28
[52] U.S. Cl. ............................ 623/16; 623/23
[58] Field of Search .......... 623/16, 18, 20, 22, 623/23

[56] References Cited

U.S. PATENT DOCUMENTS 4,888,024 12/1989 Powlan ............... 623/22

FOREIGN PATENT DOCUMENTS

| 0328848 | 8/1989 | European Pat. Off. ............. 623/23 |
| 2842847 | 4/1980 | Fed. Rep. of Germany ........ 623/23 |
| 2629337 | 10/1989 | France . |
| 0016480 | 10/1980 | Switzerland . |
| 0191182 | 8/1986 | Switzerland . |
| 2024631 | 1/1980 | United Kingdom . |
| WO89/01766 | 3/1989 | World Int. Prop. O. . |

Primary Examiner—David Isabella
Attorney, Agent, or Firm—Kenyon & Kenyon

[57] ABSTRACT

A hip joint prosthesis in the form of a femur head prosthesis or acetabulum has a mesh secured over at least part of the implant surface to define a cavity between the mesh and the supporting member of the prosthesis. The mesh is made of elastically deformable material to permit inward deformation during implantation. In addition, bone cement can be injected into the cavities so that the mesh then follows the individual shape of the cavity in the bone to mesh into the internal structure of the bone with hardened bone cement.

6 Claims, 2 Drawing Sheets

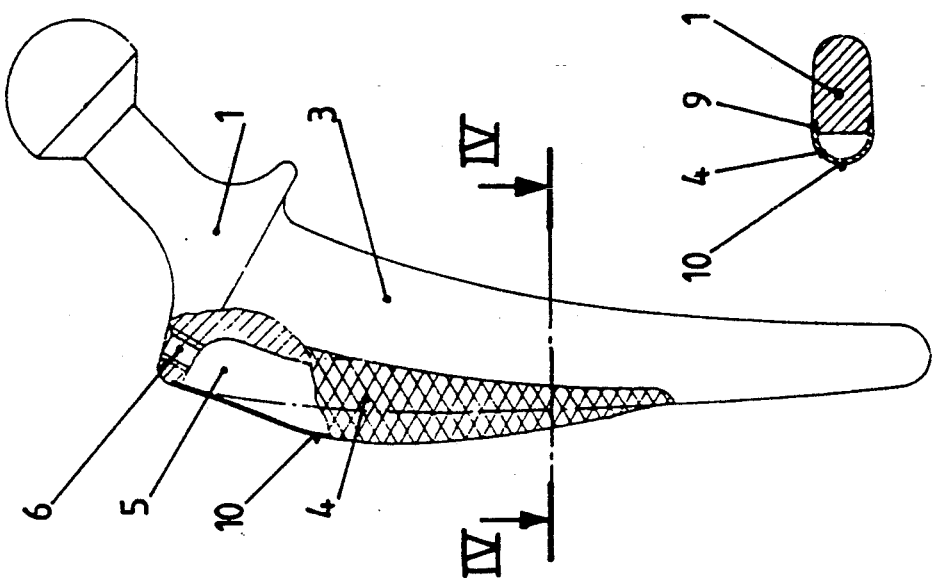
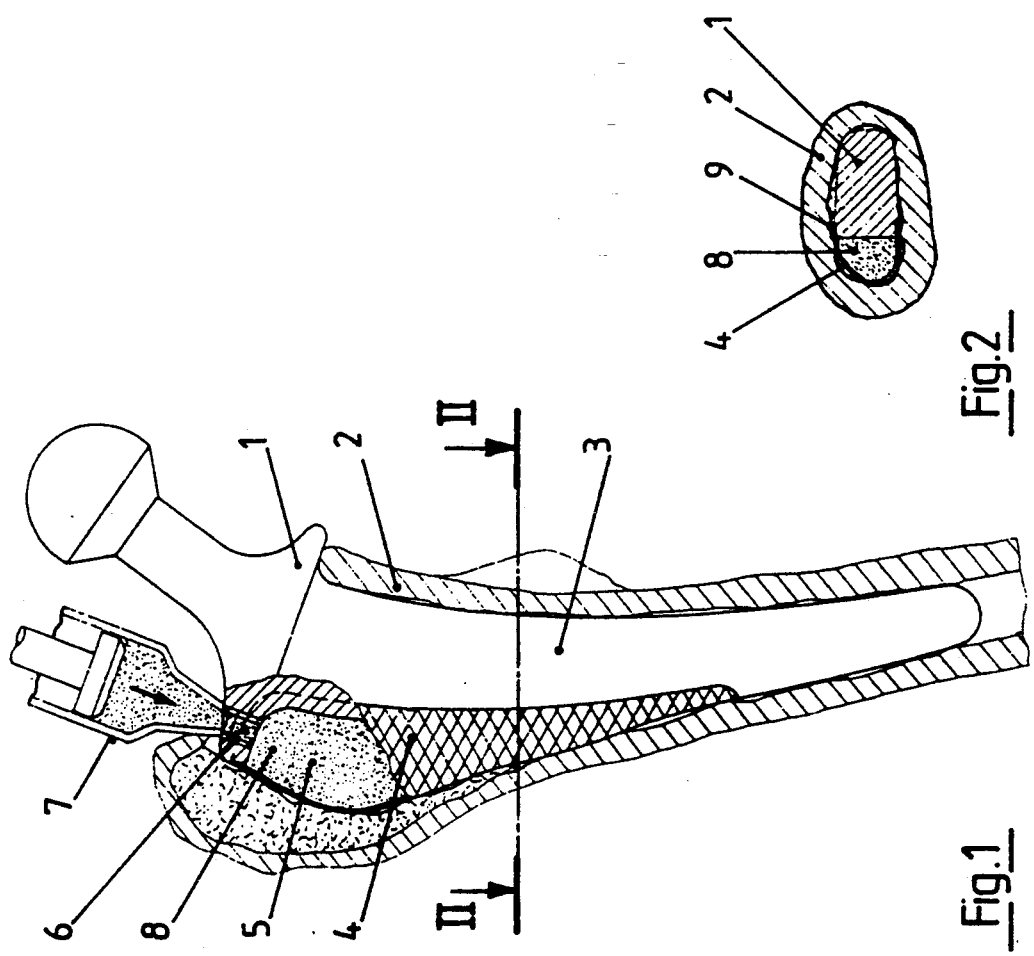

PROSTHESIS HAVING A DEFORMABLE IMPLANT SURFACE

This invention relates to a prosthesis having a deformable implant surface. More particularly, this invention relates to a hip joint prosthesis having a deformable implant surface.

As is known, implants have been constructed so as to be inserted into a bone without the use of cement. To this end, use has been made of various types of mesh structures on the implant surfaces, for example, as described in French Patent 78 19 448 in order to promote the fusion of osseous tissue on the surfaces near the bone. European patents 0 191 182 and 0 016 480 each show an attachment which is produced without the use of cement by means of the deformation of hollow bodies made from sheet metal which are subjected to internal pressure. As described, a loose stocking consisting of several layers is inserted into a prepared cavity of a femur and filled with bone cement so as to form a bed of cement for a femur head prosthesis. The stocking is constructed to be fluid-tight on the inside with the result that under internal pressure, the stocking also abuts more remote cavities. In this case, the cement is not reinforced.

French Patent 77 39 062 describes a prosthesis which is to be cemented in with contact with a bone. In this case, wire meshes are pulled up onto the shaft of the prosthesis and are placed with the prosthesis into a bed of cement. Here, the reinforcement is only effective in its predetermined thickness and at a few contact points with respect to the separating layer between the bone and the cement.

French Patent 2,629,337 describes a prosthesis of hollow construction which can be expanded by means of the injection of a liquid resin under pressure with the liquid resin subsequently hardening in place to reinforce the contour of the tubular prosthesis.

U.K. Patent Application 2,024,631 describes a prosthesis wherein a grooved pin of a prosthesis is covered over by a lattice of wire.

WO89/01766 describes a surgical support or mesh for anchoring a prosthesis and/or for reinforcing the bone cement used for anchoring a prosthesis. As described, a quiver of fibers is made for anchorage in a bone socket by means of a bone peg.

Accordingly, it is an object of the invention to produce internal meshing between ingrowing osseous tissue and the cement on the side of a prosthesis via large surfaces.

It is also another object of the invention to fill undercut grooves in a bone with cement and reinforcement in a separating layer during implantation of a prosthesis.

It is another object of the invention to provide a prosthesis with a deformable implant surface which can be readily implanted in a simple secure manner.

Briefly, the invention provides a prosthesis comprising a metal supporting member for implanting in a bone and a mesh secured to the member in order to define at least one cavity between the mesh and the member for receiving bone cement. In addition, the mesh is made of elastically deformable material in order to permit inward deformation towards the member during implantation of the member in a bone.

The mesh may be constructed as a network which forms one or several dished projecting surfaces in the outward direction away from the supporting member. The mesh may also be connected at the edges to the supporting member and is to be elastically deformable in the inward direction under inwardly acting concentrated forces.

In accordance with the invention, at least one of the supporting member and the mesh is provided with at least one opening which communicates with a formed cavity in order to permit injection of bone cement into the cavity.

During implantation, the prosthesis is able to adapt to the specific grooves in a bone without altering determined reference points of contact such that the implant becomes secured in the bone.

The supporting member may be in a form of a stem for a femur head prosthesis in which case, the mesh is disposed on a side of the stem, for example to face a greater trochanter. In another embodiment, the supporting member may be a hemispherical shell for an acetabulum.

These and other objects and advantages of the invention will become more apparent from the following detailed description taken in conjunction with the accompanying drawings wherein:

FIG. 1 illustrates a lateral elevational view of an inserted femur head prosthesis during filling of the cavities under a mesh surface with bone cement in accordance with the invention;

FIG. 2 illustrates a view taken on line II—II of FIG. 1;

FIG. 3 illustrates a lateral elevational view of the femur head prosthesis prior to implantation;

FIG. 4 illustrates taken on line IV—IV of FIG. 3;

Figure 6:
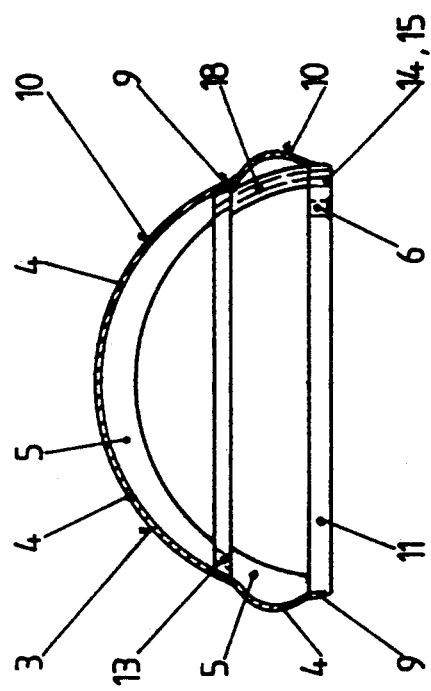
FIG. 6 illustrates a longitudinal sectional view of the acetabulum of FIG. 5 prior to implantation.

Referring to FIGS. 1 and 2, the hip joint prosthesis has a metal supporting member 1 for implanting in a femur bone 2. As indicated, the supporting member 1 has a stem or attachment surface 3 which extends along a curvilinear axis and has a recess along one side. In addition, a mesh 4 is secured to the attachment surface 3 of the member 1 over the recess in the member 1.

Referring to FIGS. 3 and 4, the mesh 4 consists of a network and has one or several dished surfaces 10 projecting in the outward direction away from the supporting member 1. In addition, the mesh 4 is connected at the edges to the supporting member 1 and is elastically deformable in the inward direction under inwardly acting concentrated forces. As shown, the mesh 4 is secured to the supporting member 1 so as to define at least one cavity 5 therebetween for receiving bone cement. To this end, a feed opening 6 is provided in the supporting member 1 in order to communicate with the cavity 5 to permit the injection of bone cement into the cavity as indicated in FIG. 1 after insertion of the implant.

As indicated in FIG. 4, the mesh 4 is structurally bonded as by welding, at the edges 9 to the member 1.

When inserting the prosthesis into a prepared cavity in the bone 2, the dished projecting surfaces 10 of the mesh 4 spring back if they encounter obstacles and follow the wall of the cavity in the bone 2. In this case, the mesh 4 abuts the bone 2 within broad limits. This abutment is reinforced if the mesh 4 is largely impervious to pasty substances and bone cement is injected through the feed aperture 6 into the cavity 5 under the mesh 4.

As indicated in FIG. 2, after the prosthesis has been inserted into the bone 2, and injection device 7 can be connected with the feed aperture 6, which may be threaded to engage with an external thread on the injection device 7. Thereafter, bone cement can be injected into the cavity 5 to secure the mesh 4 against the interior of the bone 2.

The mesh 4 thus follows the individual shape of the cavity in the bone 2 and is meshed on the inside directly into the internal structure of the bone with the hardened bone cement. At the same time, fresh osseous tissue can grow from the bone side by way of the narrow residual gaps and fuse into the remaining mesh structure. Consequently, the mesh assumes the function of a coupling between the osseous tissue of the bone 2 and the bone cement 8 within the cavity 5. As such, the cement 8 serves to transmit the compressive forces as well as forces which are tangential to the mesh 4.

The deformable mesh surfaces 10 are disposed in a geometric pattern to fill undercuts in the bone cavity and to wedge the prosthesis at right angles to the direction of extraction. As illustrated in FIG. 1, the adaptable mesh 4 is disposed on the side of the prosthesis which faces the greater trochanter while the surface on the opposite side of the prosthesis provides an unchanged reference surface for alignment purposes.

Figure 5:
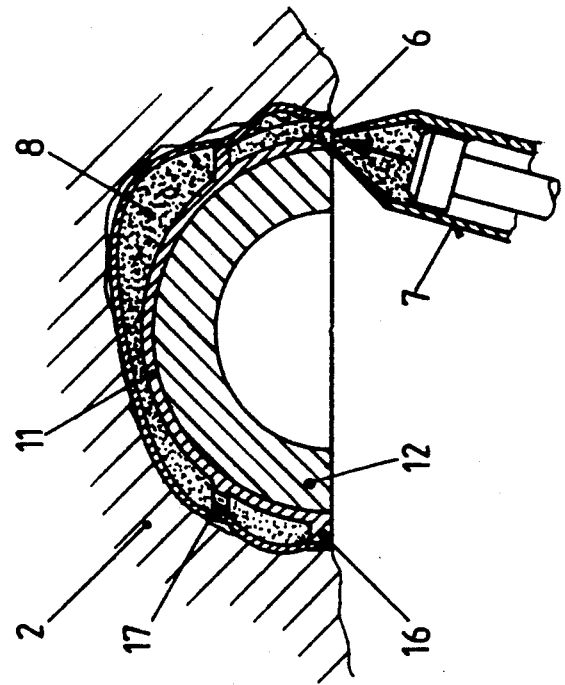
FIG. 5 illustrates a longitudinal sectional view of an acetabulum construction in accordance with the invention during implantation.

Referring to FIGS. 5 and 6, the prosthesis may be constructed as an acetabulum in order to be implanted into a pelvic bone 2.

As shown in FIG. 6, the acetabulum has a metal supporting member 11 which forms a supporting shell and a mesh 4 secured to the shell 11 via annular shoulders 16, 17 which project from the shell 11. As indicated, the mesh 4 is spaced from the supporting member 11 so as to define cavities 5 therebetween. In addition, the annular shoulders 16, 17 are provided with openings 13, 14, 15 to communicate the cavities with each other and with the exterior of the acetabulum. In order to reach the innermost cavity 5 from the edge of the supporting member or shell 11, the connecting openings 14, 15 are disposed in connecting flanges 18 of the supporting shell 11.

Referring to FIG. 5, in order to insure that the cavities 5 are filled with bone cement, the bone cement 8 is injected under a determined pressure while the injection device 7 is connected with one of the feed apertures 14.

As indicated in FIG. 5, the mesh 4 forms an annular shell which serves as a reference support for the metal supporting shell 11 during the filling operation of the annulus between the annular shoulders 16, 17 with bone cement.

During implantation, the geometrically arranged dished mesh surfaces 10 of the mesh 4 can be displaced inwardly under an elastically deformable force so as to conform with the surfaces of the bone 2. Thereafter, the bone cement 8 can be injected into the cavities between the mesh 4 and the metal supporting shell 11 to completely fill the cavities 5 while at the same time directing the mesh 4 against the surfaces of the bone 2.

Instead of using the bone cements normally used, more resilient substances may also be used to fill the cavities so long as the body can tolerate these substances and so long as these substances can be inserted as pasty substances.

It is to be noted that the dished mesh surfaces 10 are geometrically arranged so that as the pressure in which bone cement 8 is injected into the cavities 5 increases, the adhesion of the mesh 4 in the osseous tissue is increased.

The mesh 4 which is utilized is largely impermeable to the pasty substance/cement which is used to fill the cavities between the mesh 4 and the supporting member 1, 11. Further, when inserting the bone cement 8, air is expelled from the cavities 5 towards the outside through the mesh 4 and/or through sealable vents 15 in the supporting members (see FIG. 6).

The injection of the bone cement 8 is performed under an adjustable pressure until the bone cement has hardened.

When the prosthesis is implanted, the mesh 4 yields at right angles to the direction of insertion and follows the wall of the bone cavity. As the mesh 4 is largely impermeable to pasty substances, when the bone cement is injected, there is a strong branching of the bone cement in the region of the mesh whereas the mesh abuts the bone within broad limits and offers a well-structured surface for the fusion of osseous tissue. Undercut grooves in the bone are also covered with meshed surfaces in this way.

The invention thus provides a prosthesis having deformable implant surfaces to facilitate the implantation of the prosthesis in a bone and the ingrowth of osseous tissue.

What is claimed is:

1. A prosthesis comprising
a metal supporting member for implanting in a bone; and
a mesh secured to said member to define at least one unencumbered cavity between said mesh and said member for receiving bone cement and to form a coupling between the bone and the cement, said mesh being made of elastically deformable material to permit inward deformation towards said member during implantation of the member in a bone, wherein said mesh has a plurality of geometrically arranged dished surfaces projecting in a direction away from said member.

2. A prosthesis as set forth in claim 1 wherein at least one of said member and said mesh has at least one opening communicating with said cavity to permit injection of bone cement into said cavity.

3. A prosthesis as set forth in claim 1 wherein said mesh is structurally bonded to said member.

4. A prosthesis as set forth in claim 1 wherein said mesh is impermeable to pasty substances.

5. A prosthesis as set forth in claim 1 wherein said member has at least one opening communicating with said cavity and a coupling means in said opening for coupling to a bone cement injection device.

6. A prosthesis as set forth in claim 1 wherein said member is a stem for a femur head prosthesis and wherein said cavity and said mesh are disposed on only a side of said stem to face a greater trochanter.

* * * * *

UNITED STATES PATENT AND TRADEMARK OFFICE
CERTIFICATE OF CORRECTION

PATENT NO. : 5,133,767
DATED : July 28, 1992
INVENTOR(S) : Otto Frey et al.

It is certified that error appears in the above-identified patent and that said Letters Patent is hereby corrected as shown below:

Column 2, line 55, change "ment." to --ment i.e. an unencumbered cavity free of any lining or the like therebetween.--

Signed and Sealed this

Fifth Day of April, 1994

Attest:

BRUCE LEHMAN

Attesting Officer   Commissioner of Patents and Trademarks